United States Patent
Jing et al.

(12) 
(10) Patent No.: US 7,245,694 B2
(45) Date of Patent: Jul. 17, 2007

(54) X-RAY MAMMOGRAPHY/TOMOSYNTHESIS OF PATIENT'S BREAST

(75) Inventors: Zhenxue Jing, Southbury, CT (US);
Loren Niklason, Hillsborough, NC (US); Jay Stein, Boston, MA (US); Ian Shaw, Yorktown Heights, NY (US);
Ken Defreitas, Patterson, NY (US);
Tom Farbizio, Patterson, NY (US);
Christopher Ruth, Danvers, MA (US);
Baorui Ren, Andover, MA (US);
Andrew Smith, Lexington, MA (US)

(73) Assignee: Hologic, Inc., Bedford, MA (US)

( * ) Notice: Subject to any disclaimer, the term of this patent is extended or adjusted under 35 U.S.C. 154(b) by 6 days.

(21) Appl. No.: 11/203,852

(22) Filed: Aug. 15, 2005

(65) Prior Publication Data
US 2007/0036265 A1 Feb. 15, 2007

(51) Int. Cl.
*A61B 6/04* (2006.01)

(52) U.S. Cl. .................................................. 378/37
(58) Field of Classification Search ............... 378/21, 378/23, 24, 25, 27, 37, 62, 203, 208
See application file for complete search history.

(56) References Cited

U.S. PATENT DOCUMENTS

2004/0109529 A1* 6/2004 Eberhard et al. ............. 378/23
2005/0113681 A1* 5/2005 DeFreitas et al. ............ 600/426

* cited by examiner

*Primary Examiner*—Courtney Thomas
(74) *Attorney, Agent, or Firm*—Cooper & Dunham LLP

(57) ABSTRACT

A breast x-ray system and method using tomosynthesis imaging in which the x-ray source generally moves away from the patient's head. The system may include an operation mode in which it additionally takes mammogram image data.

39 Claims, 9 Drawing Sheets

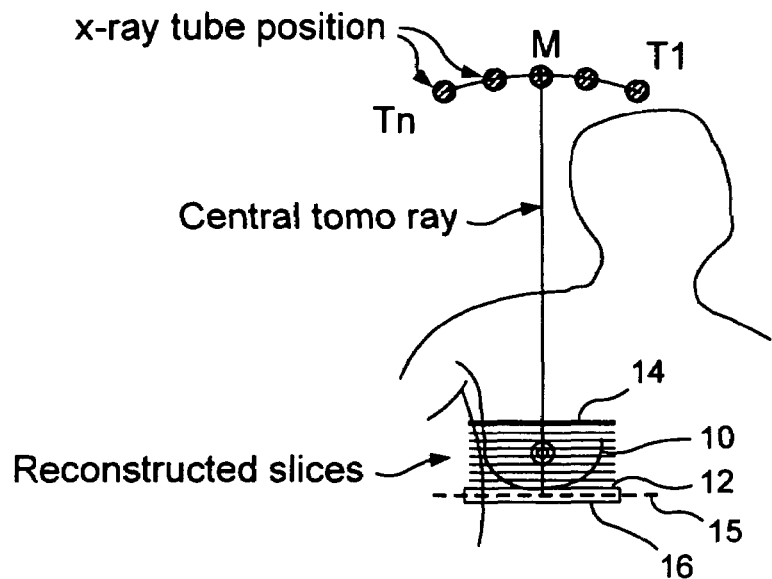
F I G. 1 (previous geometry)
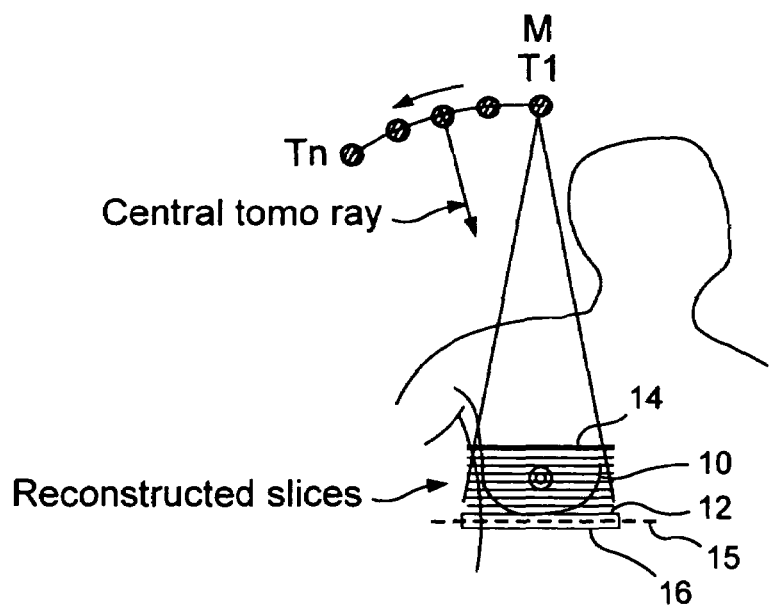
F I G. 2

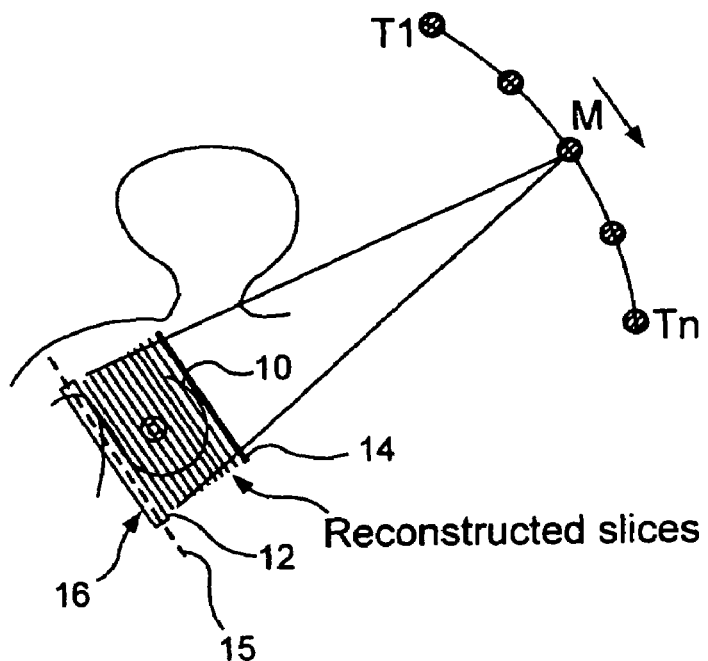
F I G. 3 (previous geometry)
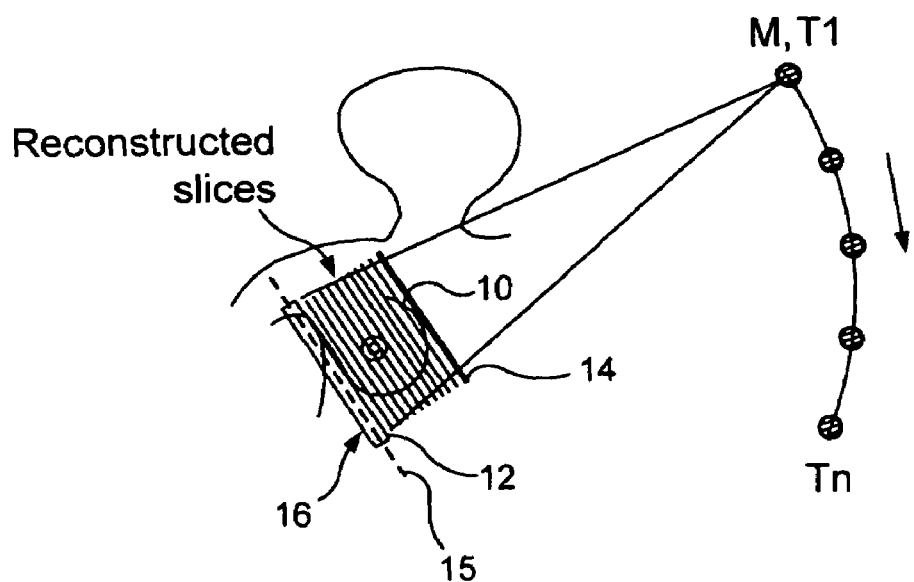
F I G. 4

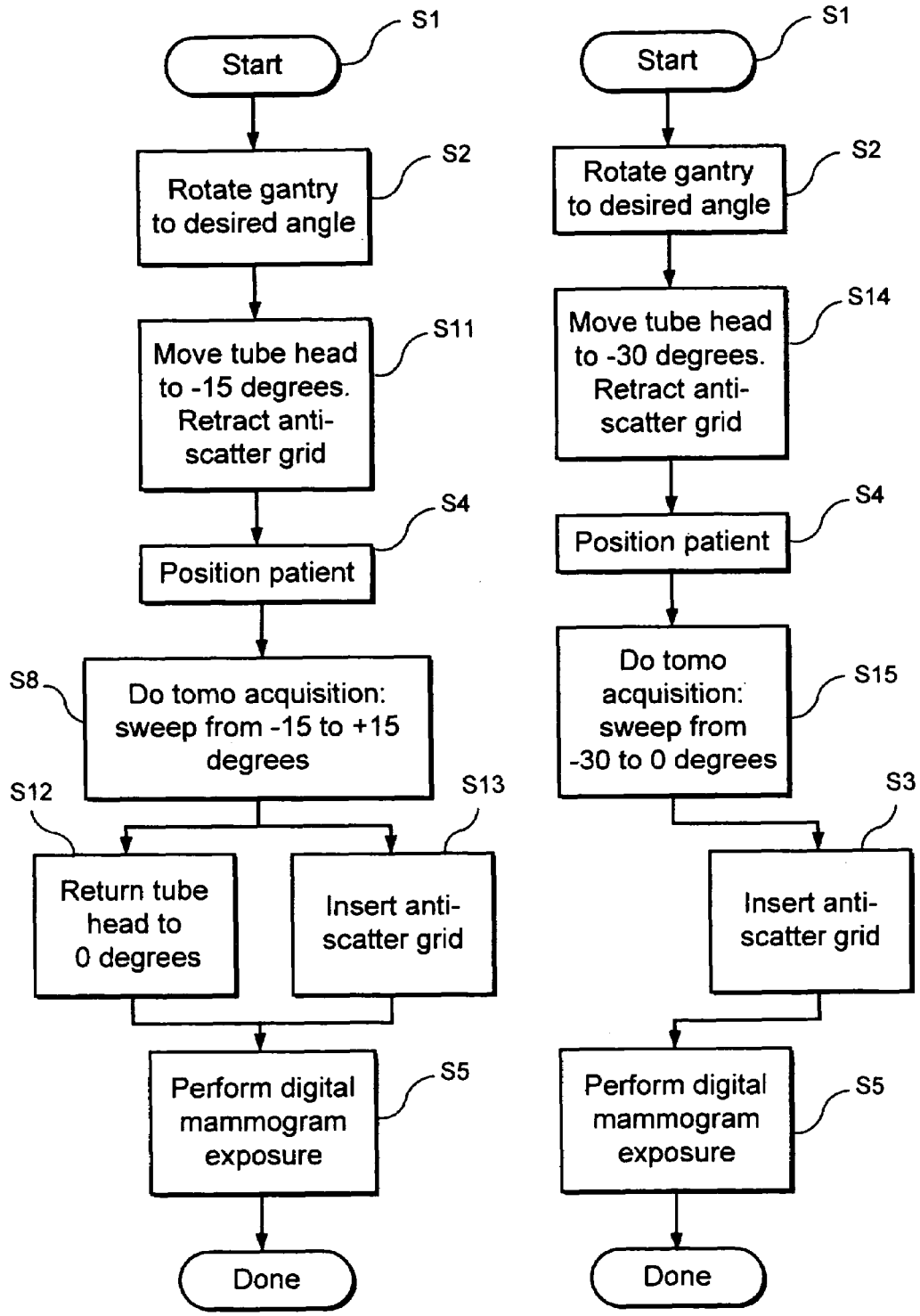

X-RAY MAMMOGRAPHY/TOMOSYNTHESIS OF PATIENT'S BREAST

FIELD

This patent specification is in the field of x-ray imaging of a patient's breast and pertains more specifically to obtaining mammograms and/or tomosynthesis images using a geometry in which the x-ray source moves over a trajectory that is generally to one side of a normal to the breast platform, and to improved shielding of the patient's head and to image acquisition, processing and display improvements.

BACKGROUND

Breast cancer and other breast lesions continue to be a significant threat to women's health. X-ray mammography currently is the most widely used tool for early detection and diagnosis, and is the modality approved by the U.S. Food and Drug Administration to screen for breast cancer in women who do not show symptoms of breast disease. A typical x-ray mammography system compresses and immobilizes a patient's breast on a breast platform positioned between an x-ray source and an x-ray imager, and takes a projection x-ray image (called here a conventional mammogram or simply mammogram) using a collimated cone or pyramid beam of x-rays at appropriate factors such as mA (current), kVp (voltage) or keV (energy), and mS (exposure time). In the United States, typically two views are taken of each breast, one from above (cranial-caudal, or CC, generally at a 0° angle—with the breast platform essentially horizontal and the x-ray beam axis normal to the platform) and one from the side (mediolateral-oblique, or MLO, at an angle of typically around 45°). Different typical views may be taken in other countries. The x-ray source typically is an x-ray tube operating at or in the neighborhood of 25 kVp, using a molybdenum or rhodium rotating anode with a focal spot of about 0.3–0.4 mm and, in some cases, 0.1 mm or less. An anti-scatter grid between the breast and the imager can be used to reduce the effects of x-ray scatter. Separately for each view, the breast is compressed to reduce patient motion and also for reasons such as reducing scatter, separating overlapping structures in the breast, reducing the x-ray thickness of the imaged breast and making it more uniform, and providing more uniform x-ray exposure. Traditionally, the imager has been a film/screen unit in which the x-rays impinging on the screen generate light that exposes the film. Currently, electronic digital flat panel array receptors are replacing the film/screen units in mammography systems. A Selenia™ digital mammography system with such a digital flat panel x-ray receptor or imager is offered by Lorad, a division of the assignee hereof, Hologic, Inc. of Bedford, Mass. Digital mammography has significant advantages and in time may fully supplant film/screen systems. Additional information regarding digital mammography systems and processes offered by the common assignee can be found at <www.hologic.com>.

Mammograms, whether from film/screen units or from digital flat panel imagers, are difficult to read, and the challenge of false negatives and false positives continues to be significant. Many advances have been made in recent years in image acquisition and in image processing, but a need still remains to reduce the rates of false negatives and positives, at least in screening mammography. Additional information can be gained through modalities such as CT and MRI, but examination and interpretation time, and cost and other factors, have limited their use in screening for breast cancer. Ultrasound breast examination has been proposed as an adjunct to x-ray examination, providing synthesized ultrasound images of thick slices of the breast that simulate the same projection view as an x-ray view and are displayed together with the x-ray view, and a unit taking both x-ray and ultrasound images has been proposed and is believed to be available at least for clinical testing. See, e.g., Patent Application Publication No. U.S. 2003/0007598 A1 and U.S. Pat. No. 5,983,123. Further, digital tomosynthesis has been proposed for x-ray breast imaging, and a laboratory unit is believed to have been installed in the U.S.A., as reported in Wu, Tao, 2002, *Three-Dimensional mammography Reconstruction Using Low Dose Projection Images*, PhD thesis, Brandeis University, incorporated here by reference. The assignee hereof has exhibited a breast tomosynthesis system at a trade show in November 2003 and November 2004, and has carried out clinical testing. See, also, Patent Application Publication No. 2001/0038681 A1 and PCT application International Publication No. WO 03/020114 A2 published Mar. 13, 2003, both incorporated herein by reference. Digital tomosynthesis in more general contexts also has been proposed. See, e.g., U.S. Pat. Nos. 6,885,724, 6,289,235 and 5,051,904, commonly assigned U.S. Pat. No. 4,496,557 and published patent applications US 2004/0109529 A1, US 2004/0066884 A1, US 2005/0105679 A1, US 20050129172A1, and Digital Clinical Reports, Tomosynthesis. GE Brochure 98-5493, 11/98, all incorporated herein by reference. Reference markers can be used in x-ray imaging for purposes such as checking the rotation angle and unwanted shift of center of rotation of an x-ray source and receptor (imager), and fiducial phantoms can be used in 3D angiography to calibrate for irregular scan geometries. See, e.g., U.S. Pat. Nos. 5,051,904, 5,359,637, and 6,289,235, N. Navab, et al., *Dynamic geometrical calibration for 3D cerebral angiography*, SPIE Vol. 2708, pp. 361–370, and said PCT published application WO 03/020114 A2, all incorporated by reference here.

A tomosynthesis system specifically for imaging patients' breast is disclosed in commonly owned published U.S. patent application No. US2004/0101095A1, which is hereby incorporated by reference here. In known tomosynthesis breast units, it is believed that the motion of the x-ray source typically is symmetrical relative to a line from the focal spot of the x-ray source to the breast platform and perpendicular to the platform. For example, the source generally moves through an angle of ±15° or ±30°, where 0° corresponds to the position for the CC or MLO mammogram view. One of the references identified above, U.S. Pat. No. 6,885,724, discusses asymmetric geometry in the context of a table or wall configuration where the room dimensions may preclude a fully symmetrical scan, and proposes modifying the typically symmetrical scan such that the sweep on one side of a 0° position is not the same as the sweep on the other side, so as to accommodate room size limitations.

SUMMARY OF THE DISCLOSURE

In known breast tomosynthesis, which involves acquiring a sequence of x-ray exposures at varying angles about a compressed and stationary breast of a patient, the motion of the x-ray source typically proceeds in an arc symmetrically about the normal to the breast platform. Following the scan, the 3-D image is reconstructed into cross-sectional slices that typically are parallel to the breast platform. It has been discovered that the motion of the x-ray source in this approach, at least for positions that include the CC position, may raise concerns of patient comfort, patient safety and patient motion artifacts. For example, if a scan that includes the CC position starts when the x-ray source is away from and moves toward the patient's shoulder, this typically would require the patient to cock her head away at the start of the scan and during positioning of the breast, which may be uncomfortable or not even possible for some patients. In addition, motion of the patient's body in the course of cocking the head away and possible moving the head during the scan away from an uncomfortable position, may introduce motion of her breast relative to the x-ray imager and consequent motion artifacts in the image. If the starting position is away from the patient's head, so that the x-ray source moves toward the patient's head during the scan, and a shield is used to position her head outside the x-ray source path, the patient may be startled by the approach of the x-ray source and move, with consequent possibility of motion artifacts in the image. If there is no shield in such a scan, the patient may have to cock her head rapidly during the scan to avoid contact, with increased discomfort and likelihood of motion artifacts, or else the patient would require her head to remain cocked throughout the scan so as to avoid contact as the source approaches the end of the scan. Even if a shield is used, the patient may have to cock her head to one side so as to avoid the head hitting the shield.

An additional challenge relates to using the same equipment for both tomosynthesis imaging and mammogram imaging. One known method to perform both imaging in the same scan is to acquire the mammogram data in the middle of a tomosynthesis scan. If a single scan is used, the x-ray source would be slowed down and stopped for the mammogram data acquisition, then re-started and moved to the remaining tomosynthesis data positions, assuming a stop-and-shoot technique is used. If a continuous scan is used, then some provisions would be made to account for the fact that typically the patient x-ray dose for a tomosynthesis data acquisition at any one imaging position is much lower than that for a mammogram data acquisition. If the mammogram data acquisition is done separately from the scan for tomosynthesis data acquisition, e.g., before or after the scan for tomosynthesis data, the time to position the equipment for mammogram data acquisition and separately for tomosynthesis data acquisition may unduly increase the examination time.

Yet another challenge arises if an anti-scatter grid is used for mammogram data acquisition but not for tomosynthesis data acquisition. In that case, the time for moving the grid into the x-ray beam before taking the mammogram data and out of the x-ray beam before taking subsequent tomosynthesis data, also should be taken into account.

Yet another challenge concerns the use of a patient shield. Because the x-ray tube head moves during a tomosynthesis scan, some method of preventing accidental patient contact should be developed. One known solution is to house the x-ray tube assembly in a large enough housing to enclose the x-ray tube and accommodate its motion inside the housing, which does not move during the scan. One problem with this approach is that the housing will be rather large. If there is a separate shield in front of the tube, or between the tube's scanning path and the patient's head, then known solutions present problems in requiring the patient's head to cock to one side to avoid pressing against the shield, and additionally the shield can prevent convenient access to the patient's breast and the breast compression hardware, presenting difficulties for the mammographic technologist when positioning the patient.

The new approach taught in this patent disclosure substantially overcomes these and other known issues by moving the x-ray source differently—through a trajectory that generally does not require the patient to cock her head even when the trajectory includes the CC position, or involves minimal tilting of the head. A patient shield is described which is a preferred design to use with this different acquisition geometry. The patient shield is small, and is also preferably is designed to shift, to accommodate different acquisition geometries for left and right breast imaging, and to shift out of the way to facilitate access for patient positioning and adjustment of the breast on the breast platform. Other features and benefits of the new approach will become apparent from the detailed description below.

Yet other aspects of the new approach involve image acquisition and processing improvements in which the output of pixel locations in the imager may be selectively binned, for example by binning in only one direction or binning differently in different directions or binning for tomosynthesis images but not for mammograms or differently between tomosynthesis images and mammograms. Other aspects involved display improvements, including but not limited to overlapping mammograms and matching tomosynthesis images that may or may not be obtained from the same compression of the breast.

BRIEF DESCRIPTION OF THE DRAWING

FIG. 1 illustrates a previously disclosed geometry for right breast x-ray tomosynthesis data acquisition alone and, in the alternative, when combined with CC mammogram data acquisition.

FIG. 2 illustrates a new geometry for right breast x-ray data acquisition that can also include CC mammogram data acquisition and typically but not necessarily moves the x-ray source away from the patient's head without requiring the patient to cock her head to accommodate the x-ray source trajectory or involves minimal head tilting.

FIG. 3 illustrates previously disclosed geometry for right breast tomosynthesis data acquisition alone and, in the alternative, when combined with MLO mammogram data acquisition.

FIG. 4 illustrates a new geometry for right breast x-ray data acquisition that can also include MLO mammogram data acquisition.

FIGS. 5 through 8 are conceptual flowcharts illustrating processes for taking mammogram image data and tomosynthesis image data in different sequences.

DETAILED DESCRIPTION OF PREFERRED EMBODIMENTS

Figures 5, 6:
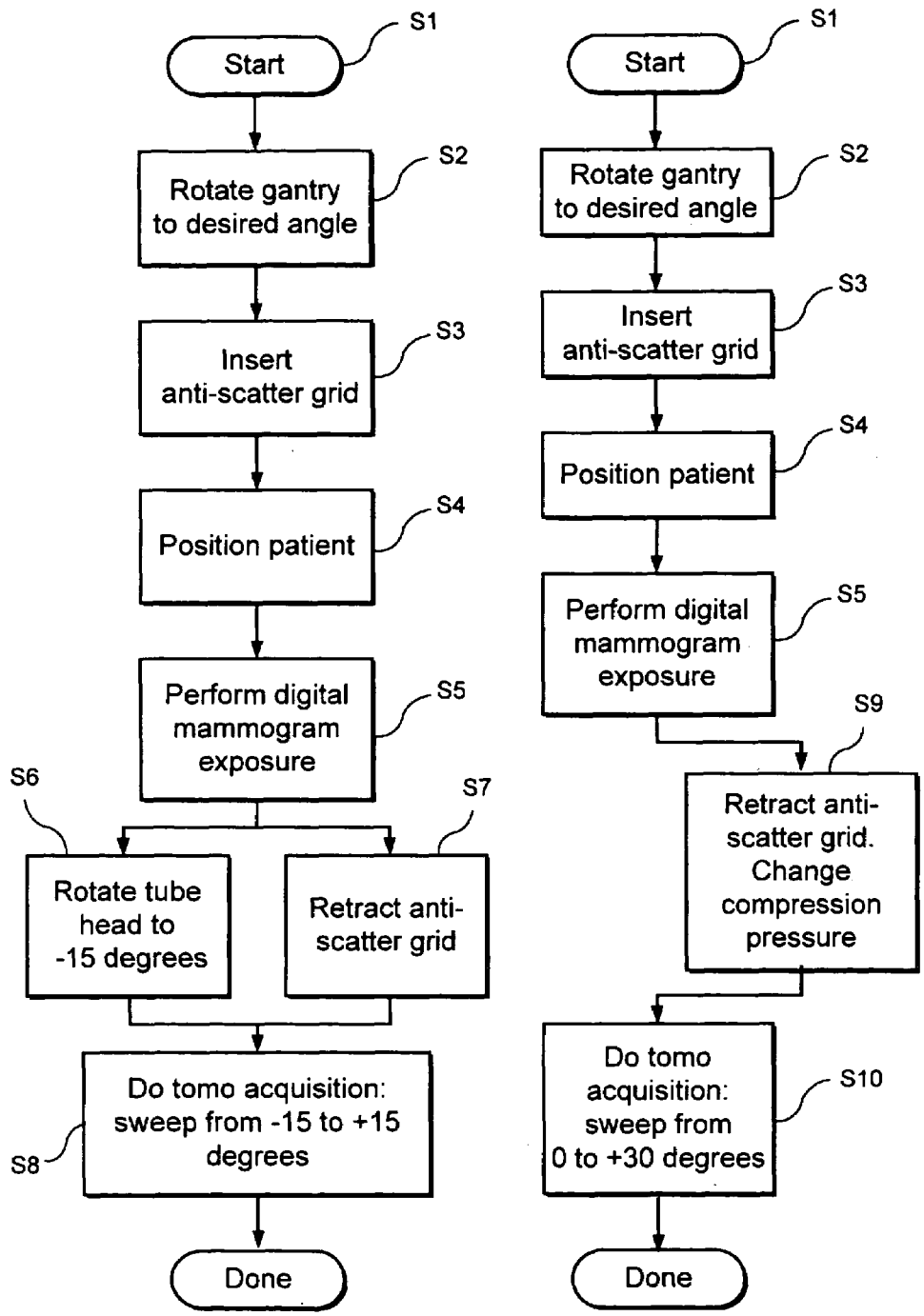

In describing preferred embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

FIGS. 1 and 2 illustrate scanning geometry differences between a previously proposed system (FIG. 1) and a new system disclosed in this patent specification (FIG. 2). As illustrated in FIG. 1, a patient's right breast 10 is immobilized on a breast platform 12 with the use of a compression paddle 14, in a CC imaging position. An x-ray source such as an x-ray tube with collimation for the x-ray beam moves relative to breast 10 along a trajectory defined by points T1–Tn, for example through an arc of ±15° relative to a normal to breast platform 12, which normal coincides with the central x-ray (labeled central tomo ray in FIG. 1) at a position M. At each of a number of positions of the focal spot, indicated in FIG. 1 by points at and between positions T1 and Tn, an x-ray image of breast 10 is taken with an imager 16. While only five imaging positions are illustrated in FIG. 1, typically a greater number is used such as, for example and without limitation, 11 positions. Projection image data are taken at each of the imaging positions T1–Tn, typically at a much lower dose at each position than a conventional mammogram, and the resulting image data are processed as in known in the art into tomosynthesis images. Typically, the tomosynthesis images represent reconstructed slices or slabs of the breast that are parallel to the breast platform, as is illustrated in FIG. 1 by a number of lines parallel to breast platform 12. However, slices of slabs having other orientations can be reconstructed instead or in addition. As is known in the art, the slices of slabs can have selected thicknesses, and can be displayed in a variety of ways.

When operating in a combination mode, the same equipment used to acquire image data for tomosynthesis images can be used to acquire a conventional mammogram, for example from the focal spot position labeled M in FIG. 1, which may or may not coincide with one of the positions for taking tomosynthesis image data. This mode of operation will be referred to in this patent specification as 'combo' mode. The image data for the mammogram can be in addition to the image data for the tomosynthesis images. Alternatively, in addition to being used for the mammogram, the image data for position M can be used as one of the several sets of projection image data for reconstructing tomosynthesis images. As known, the data for tomosynthesis images typically is taken at a substantially lower patient x-ray dose than the data for a mammogram image. As a non-limiting example, the total x-ray dose used for acquiring all the tomosynthesis images in a scan can be approximately the same as the dose for a single mammogram. Also, preferably but not necessarily, mammogram data acquisition typically is done with an anti-scatter grid 15 between the breast 10 and imager 16 while tomosynthesis data acquisition typically is done without an anti-scatter grid in the x-ray beam that images breast 10. In a combo system, an x-ray grid 15 may be moved into the x-ray beam for a mammogram and out of the beam for tomosynthesis imaging.

As seen in FIG. 1, the x-ray source moves toward the patient's head 18 for its focal spot to move from imaging position Tn to imaging position T1. It typically is necessary for the patient to move her head out of the way for the x-ray source to move to imaging position T1 in FIG. 1. The sight of the approaching massive x-ray source can be disconcerting, particularly in the already stressful setting of the x-ray examination, and for some women the necessary movement of the head and upper body can be physically demanding. If the x-ray source is moving in the opposite direction, from position T1 to position Tn, the patient may still involuntarily react by moving her head from a cocked to a more relaxed position and thereby possibly changing the position of breast 10 relative to imager 16 and thus introducing motion artifacts in the imaging process. The issue of patient motion and head cocking and upper body motion might be even more severe in the situation where Tn is the first exposure position and T1 the last in a tomosynthesis scn, because the x-ray tube will be moving towards the patient during the scan.

In contrast, in the new approach illustrated in FIG. 2 the x-ray source generally moves over a trajectory that is to one side of the patient's head even for CC imaging, e.g. away from the patient's head, and does not require cocking the patient's head during the scan or involves at most minimal cocking. The scan starts from focal spot position T1 that in this example is much further, and is laterally offset, from the patient's head than position T1 in FIG. 1 and corresponds, for example, to position M in FIG. 1. From this position T1 in FIG. 2, the x-ray source moves further away from the patient's head, in the direction of the arrow seen in the Figure, through a number of other imaging positions indicated by dots, to position Tn. As with the arrangement of FIG. 1, tomosynthesis data can be taken at each of the imaging positions, which can be, and typically are, more than the five illustrated in the Figure, and the data are used to reconstruct tomosynthesis slice images. These slices can have selected thicknesses, and can be parallel to imager 16, as illustrated in FIG. 2, or can be at other orientations, and can be displayed in a manner comparable to that discussed above for the images obtained with the FIG. 1 arrangement.

In the FIG. 2 geometry, the image data taken at position T1 can be used to form only a tomosynthesis image, or only a mammogram image, or both a tomosynthesis image and a mammogram image.

The imaging position labeled T1 in FIG. 2 also is labeled M to indicate that it can also, or alternatively, be an imaging position for mammogram data acquisition. Because in this example mammogram data can be acquired before the tomosynthesis scan starts, or at least at a time coinciding with the start of the tomosynthesis scan, the use of an anti-scatter grid for acquiring mammogram but not tomosynthesis data is simplified and made more practical. In this case, the grid can be in position before the breast is compressed, so no time would need to be taken for that while the patient's breast is being compressed, and the patient is spared hearing and perhaps feeling the grid moving-in operation. In addition, if the grid is to be retracted for the subsequent tomosynthesis data acquisition, this can be done concurrently with another operation, such as some reduction in breast compression after the mammogram is taken.

The nature of tomosynthesis data reconstruction is such that the tomosynthesis data acquired with the geometry of FIG. 2 also can be reconstructed into images of slices parallel to the image plane of imager 16, as illustrated by means of a series of parallel lines in FIG. 2. The slices can be of any desired thickness and number, and can be at other orientations if desired.

An alternative is to take the tomosynthesis data first, starting with imaging position T1 and ending with imaging position Tn, then returning the x-ray source to position M, which can but need not be the same as position T1, and taking mammogram data, possibly after first moving anti-scatter grid 15 in position between breast 10 and imager 16. The operation of moving the anti-scatter grid 15 into position can occur concurrently with the return of the x-ray tube from location Tn to M, thereby reducing the time needed for the entire examination. The alternate method of taking tomosynthesis data first and the mammogram second, might offer advantages in overall image quality due to reduced blurring caused by patient motion. Typical x-ray exposures for mammograms are shorter than 1 second, while tomosynthesis scans are typically longer than this, perhaps 1 to 10 seconds. In a preferred operational scenario, the patient is asked to hold her breath just prior to the start of the scan. If the tomosynthesis acquisition occurs before the mammogram, then even if she cannot hold her breath for the entire procedure, she might be able to hold her breath until at least the tomosynthesis image acquisition is completed. Patient breathing causes less of a blurring problem for the mammogram exposure because of its shorter duration.

Yet another alternative is to start the scan at imaging position Tn and move the x-ray source toward position T1 while taking tomosynthesis image data and, if desired, take a mammogram image data at imaging position M. Although this involves moving the x-ray source toward the patient's head during the scan, it still requires no head tilting or minimal tilting, and the possibility of startling the patient can be reduced by using appropriate shielding, for example as discussed below in connection with FIGS. 13–16.

FIGS. 3 and 4 are similar in concept to FIGS. 1 and 2, respectively, but illustrate imaging the right breast from positions that include the MLO position. In the previously proposed geometry illustrated in FIG. 3, the MLO position for taking mammogram data is in the middle of the tomosynthesis scan that starts from position T1 and ends at position Tn. Moreover, the x-ray source at position T1 is closer to the patient's head than in position Tn. In other respects, the geometry of FIG. 3 is similar to that of FIG. 1. Again, the tomosynthesis data can be used to reconstruct slices at desired orientation and of desired thicknesses, and an example of an orientation parallel to imager 16 is illustrated in FIG. 3.

In contrast, in the new geometry illustrated in FIG. 4 the tomosynthesis scan can start at the imaging position closest to the patient's head and then move away from the patient's head. The starting position T1 may coincide with, or can be close to, a position M for taking mammogram data in an MLO image. In other respects, the operation of the FIG. 4 geometry is similar to that of FIG. 2. Again, the mammogram data at position M can be taken before the tomosynthesis scan, and after the tomosynthesis scan is completed the x-ray source can be returned to position M for taking mammogram data and, as an alternative, the scan can start at imaging position Tn.

The imaging positions and scan motion for imaging the left breast are a mirror image of those illustrated in FIGS. 2 and 4 for the right breast, relative to a vertical symmetry plane that is perpendicular to the drawing sheet and bisects the patient. Of course, if the x-ray source in FIG. 2 moves to the right of the patient when imaging the right breast, it would move to the left of the patient when imaging the left breast. Similarly, while the x-ray source can move generally down along the left side of the patient in FIG. 4 to image the right breast, it can move generally down along the right side of the patent to image the left breast. And, it should be understood that the principle of moving the x-ray source over a trajectory that is generally away from the patient's head is applicable when it includes mammogram data acquisition positions other then the CC and MLO positions. It should be further understood that the M and T1 position need not be the same, and that the T1 position can be closer to the patent's head than as illustrated in FIGS. 2 and 4, so long as it is significantly further than the T1 position of FIGS. 1 and 3, respectively and does not raise the issues raised in the geometry of FIGS. 1 and 3, particularly those raised in the FIG. 1 geometry.

FIGS. 5 and 6 are conceptual flowcharts comparing operation of the geometry of FIG. 1 or 3 with that of FIG. 2 or 4. In both FIGS. 5 and 6, digital mammogram data acquisition takes place before taking data for tomosynthesis images. In FIG. 5, using the previously proposed geometry of FIGS. 1 and 3, the first operation after the process starts at step S1 is to rotate the gantry that carries the x-ray source to a desired relative 0° angle for mammogram imaging, e.g., for a CC mammogram or an MLO mammogram (which can be absolute 0° for CC and absolute 45° for MLO relative to a vertical axis in the room). At S3, an anti-scatter grid is inserted, and at S4 the patient is positioned and the patient's breast is compressed. At S4 a digital mammogram exposure is carried out and the data is processed for or into a mammogram image. The next two steps can be performed concurrently and involve rotating the x-ray source at S6, e.g. to a position that is −15° from the relative 0° position for the mammogram data acquisition, and retracting the anti-scatter grid at S7. At S8, tomosynthesis data acquisition is carried out as previously proposed, e.g., over a sweep angle from −15° to +15°.

In FIG. 6, using the new geometry of FIG. 2 or 4, the process is simplified and speeded up. Some of the steps are the same as in FIG. 5, and bear the same step designations—steps S1 through S5. However, in the process of FIG. 6, there is no need for step S6, and instead of simply retracting the grid as in S7, the process of FIG. 6 can additionally and optionally reduce breast compression in step S9. In step S10, the process of FIG. 6 carries out a tomosynthesis data acquisition sweep from the 0° to e.g. +30°, moving generally in a direction away from the patient's head. In the alternative, the process can be adapted to start at the imaging position away from the patient's head, e.g. at +30° and end at the relative 0° imaging position.

FIGS. 7 and 8 summarize a different process that carries out tomosynthesis data acquisition first and a mammogram data acquisition second. The process of FIG. 7 uses the previously proposed geometry of FIG. 1 or 3. Some of the steps are the same as the correspondingly numbered steps of FIG. 5—steps S1, S2, S4, S5 and S8. Step S11 is different and involves moving the x-ray source to a position some distance away from the desired CC or MLO relative 0° position, e.g. to a −15° position. Step S12 also is different—it involves returning the x-ray source to the 0° position because it follows step S8, in which a tomosynthesis scan is carried out, e.g. by moving the x-ray source from −15° to +15°. Step S13 involves inserting an anti-scatter grid before taking digital mammogram data at step S5. FIG. 8 illustrates similarly doing tomosynthesis data acquisition first and mammogram data acquisition second, but with the new geometry of FIG. 2 or 4. In FIG. 8, again some of the steps are the same—S1, S3, S4 and S5. However, here S14 follows S1 and involves moving the x-ray source some distance away from the CC or MLO position, i.e. away from the relative 0° position, e.g. to a −30° position away from the patient's head. In addition, after the patient is positioned at S4, step S15 involves doing a tomosynthesis data acquisition sweep toward the 0° position, e.g. from −30° to 0°, then inserting the anti-scatter grid at S3 and doing mammogram data acquisition at S5.

Figure 9:
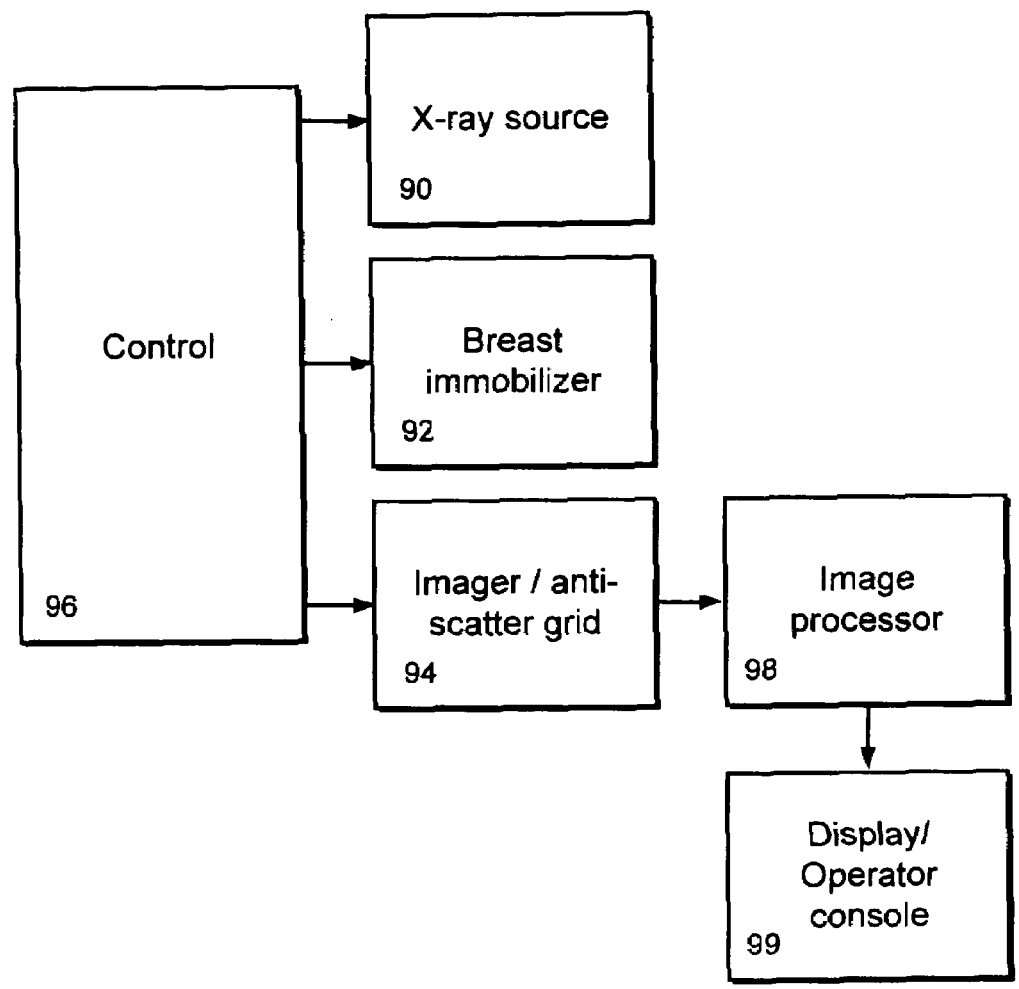
FIG. 9 is a general block diagram illustrating a mammography/tomosynthesis system for practicing the new approaches disclosed in this patent specification.

FIG. 9 illustrates, in general block diagram format, a mammography/tomosynthesis system that can implement the new features described in this patent specification, including those discussed in connection with all other figures. An x-ray source 90, a breast platform mechanism 92, and an imager/anti-scatter grid unit 94 are controlled for movement and functionality by a control 96. Image data from imager/grid unit 94 are processed by image processing unit 98 and displayed at display and interface unit 99 in a desired format and in a manner required by a health professional.

Figure 10:
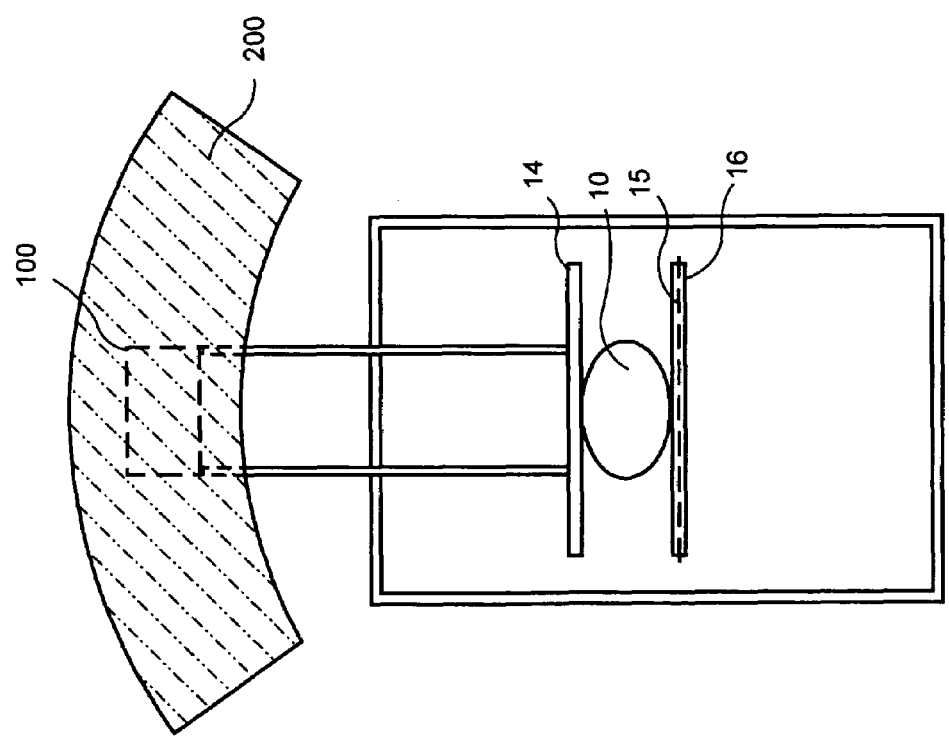
FIG. 10 illustrates a previous method of shielding the patient from the motion of the x-ray source.

Because of the motion of the x-ray tube during the tomosynthesis scan, an important safety and patient comfort design goal is to avoid contact of the patient with the moving mechanics and avoid patient discomfort. Further improvements are possible to the known methods of designing face shield for systems using the novel scanning geometry illustrated in this patent specification, and these relate primarily to patient comfort and ease of patient positioning. A known method, as in published U.S. patent application US 2005/0129172A1 is to encase the x-ray source in a large enough housing so as to allow the full required motion range of the x-ray tube during tomosynthesis imaging to place within the housing. Such a design results in a very large system. An alternate known method is to have a large external shield placed over the x-ray tube, positioned between the patient and the moving x-ray tube. This is illustrated in FIG. 10. The shield 200 protects the patient from contact from the x-ray source 100 as the source moves during the tomosynthesis acquisition.

If the distance between the breast compression plates and the x-ray tube is sufficiently large, then it may not be necessary to have the shield cover the x-ray tube—a shield below the x-ray tube can provide adequate patient collision protection.

Figure 11:
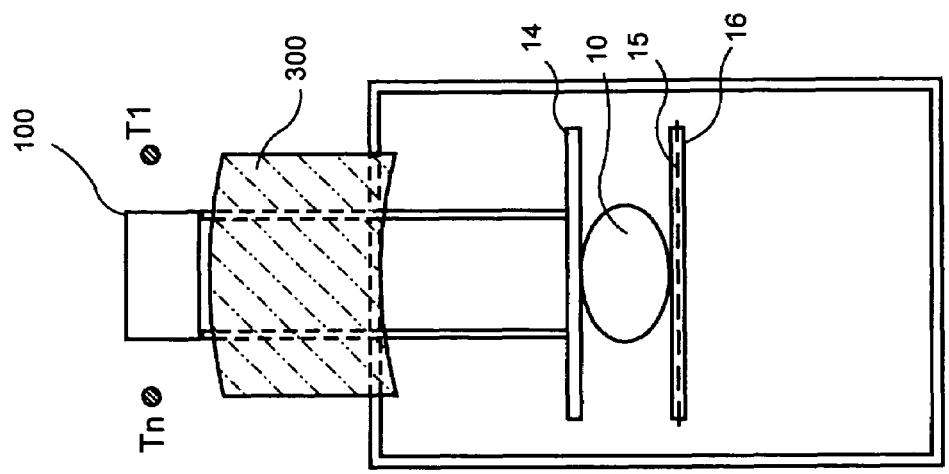
FIG. 11 illustrates a new method for shielding the patient from the motion of the x-ray source.
Figure 12:
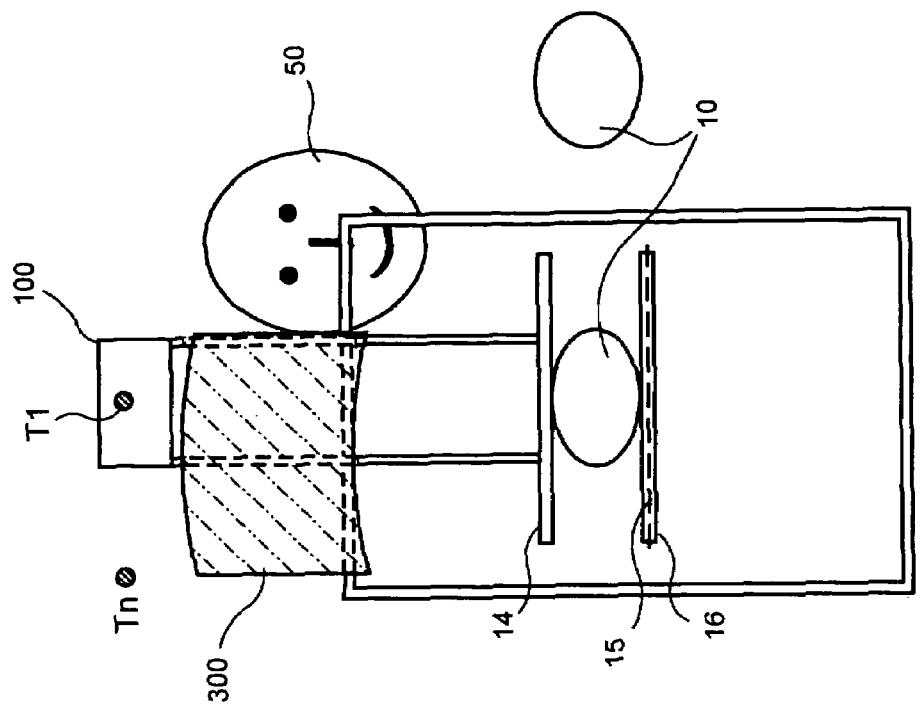
FIG. 12 illustrates patient head placement when the shield is used for a tomosynthesis examination in which the x-ray source's angular sweep is substantially symmetric about a normal to the breast platform.

While typical mammography source-to-imaging-plane distances (SID) are in the range of about 65–66 cm, an SID greater than about 70 cm can prevent patient contact and contribute to patient comfort. FIG. 11 illustrates such geometry of SID greater than about 70 cm, allowing for a shield 300 to be below the actual x-ray source 100 and to protect the patient's head from contact with moving parts as the x-ray source moves from location T1 to Tn, or from Tn to T1. Shield 300 preferably has a horizontal portion that fits between the top of the patient's head and the moving x-ray source, and a generally vertical part that can fit in front of or behind the patient's head, and generally is made of a transparent or at least translucent material. FIG. 12 illustrates the position of the patient's head 50 when using shield 300, for a scan whose angles are symmetric about the normal to the breast platform. To avoid hitting the shield, the patient's head needs to be cocked to one side. This is possibly an uncomfortable position and may result in undesirable patient motion during the procedure, which can deteriorate image quality.

Figure 13:
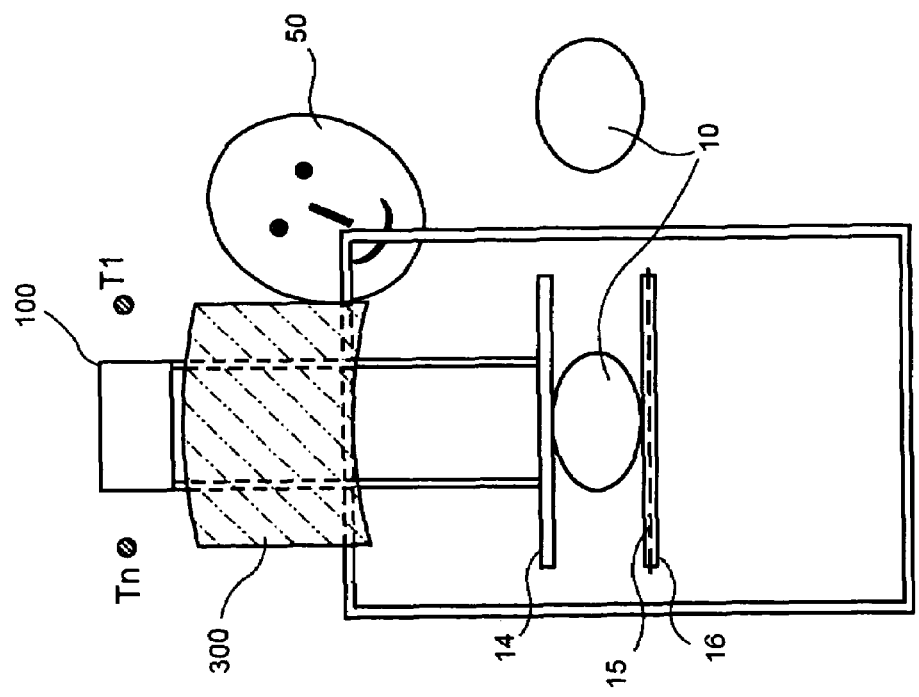
FIG. 13 illustrates a new patient head placement when the shield is used for a tomosynthesis examination of the right in which the x-ray source's angular sweep is over a trajectory that generally is spaced from a normal to the imager in the MLO position, e.g. the source moves away from the patient's head. A mammogram image may be taken in the same sweep of the x-ray source.

FIG. 13 illustrates an improved face shield arrangement relative to that illustrated in FIG. 12, and is especially suited for x-ray examinations involving tomosynthesis scans where the x-ray tube sweeps over a trajectory that is generally to one side of the patient's head. In FIG. 13, the shield 300 can be similar in construction to that of FIGS. 11 and 12, but is mounted differently. Here shield 300 is able to move laterally, side-to-side. In FIG. 13, shield 300 is shown shifted to the left (i.e. toward the right breast of the patient) so that it is not symmetrically oriented relative to the center of compression paddle 14 and image receptor 16. This allows the patient head 50 to be in a relaxed position, or at most cocked at a significantly lesser angle than in FIG. 12. This arrangement offers good patient protection if the x-ray source motion is over a trajectory generally away from the head, as schematically illustrated by source positions T1 to Tn. Because the face shield is able to shift laterally, it can be placed to the right of the center of the compression paddle for opposite direction scans, as is illustrated in FIG. 14, thus allowing for no head cocking or at most minimal head tilting when imaging the left breast.

If the face shield does not shift laterally, it must be made larger to accommodate all possible scans. In addition to the need to cock the patient's head, the larger face shield can be aesthetically less pleasing, and its larger appearance might be intimidating to some patients.

Figure 15:
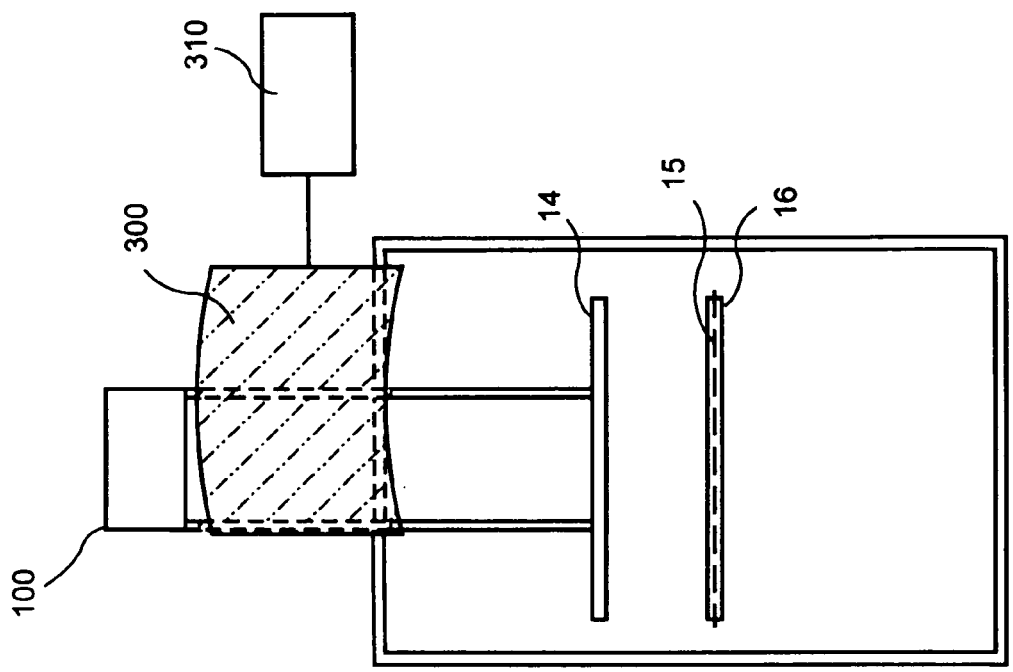
FIG. 15 illustrates a motorized method of moving the face shield.
Figure 14:
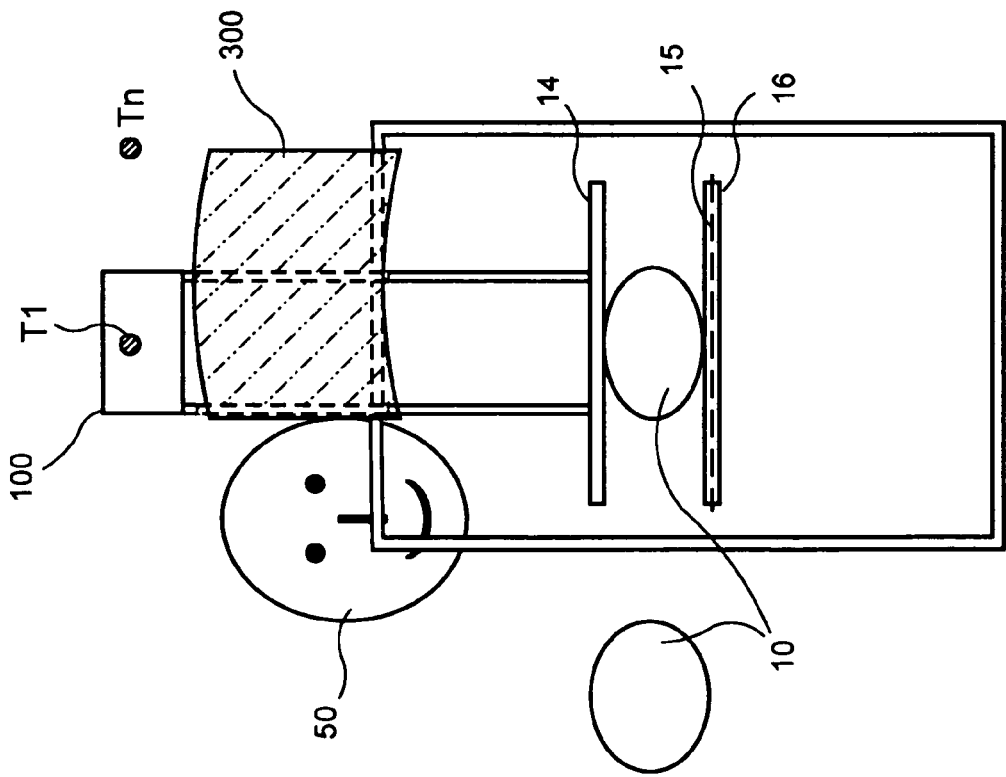
FIG. 14 is comparable to FIG. 13 but illustrates a tomosynthesis examination of the left breast.

The face shield shifting motion of the type illustrated in FIGS. 13 and 14 can be carried out in a variety of ways. Shield 300 can be manually shifted by the operator, and can slide within tracks or using some other mechanical support that allows for lateral sliding motion relative to compression paddle 14. An alternate method is through motorized means, as illustrated in FIG. 15, where a motor or actuator 310 is coupled to face shield 300 to selectively move it laterally under electronic control provided, e.g. from unit 96 or unit 99 (FIG. 9) or from another source commanded by a health professional. The motion can be initiated through switches at or near the shield, or through a human controlled computer interface. It can also occur automatically under system control, in which case it will position itself to the optimal position depending upon the examination type and patient orientation and scan direction, based on look-up data in the software operating the mammography/tomosynthesis unit.

Figure 16:
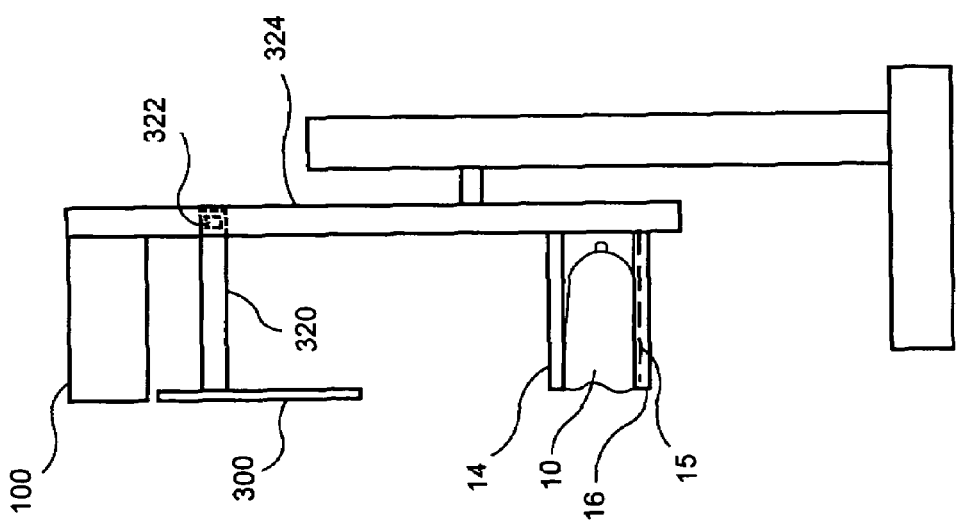
FIG. 16 is a side view of the configuration of FIG. 15.

A non limiting example of shield 300 is illustrated in FIG. 16, which is a side view of the configuration illustrated in FIG. 15. The side view shows the face shield support 320, which supports the face shield, and allows the lateral shifting of the face shield as illustrated in FIG. 15. The mounting allowing lateral shifting can be designed in several ways, including the lateral shifting of the face shield 300 relative to its support 320 along an appropriate track (not illustrated), or the lateral shifting of the shield support 320 along track 322 in support 324 for x-ray source 100, which would also cause the shifting of the shield 300 as it is attached to the support 320.

Figure 17:
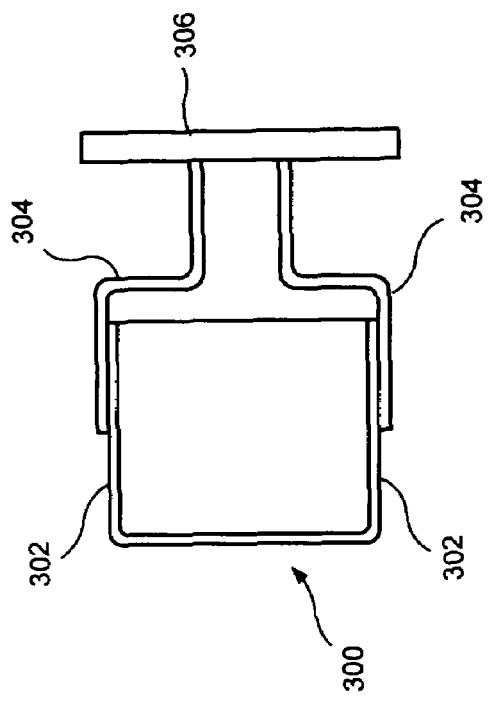
FIG. 17 is a plan view of a detail of the face shield and its supports.
Figure 18:
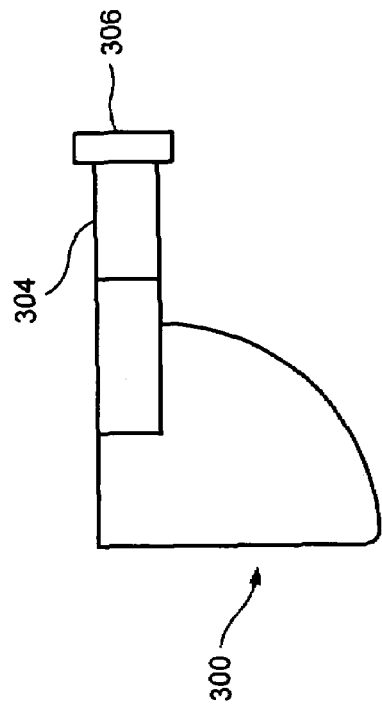
FIG. 18 is a side view of the configuration of FIG. 17.

As illustrated in FIGS. 15–18, shield 300 can comprise a generally flat pate, typically but not necessarily made of a transparent or translucent material, oriented in a generally vertical plane, and side wings 302 against which the patient's head can rest—to the right of shield 300 as seen in FIG. 13 and to the left of the shield as seen in FIG. 14. As seen in the plan view of FIG. 17, shield 300 is generally shaped as a channel section, and as seen in side view in FIG. 18, its side wings 302 can be tapered. FIGS. 17 and 18 illustrate a preferred alternative mounting of shield 300, where side wings 302 are secured to respective brackets 304 that is turn are secured to a beam 306 slidably mounted on support 324 (FIG. 16) for selective lateral movement that position shield 300 as seen in FIG. 13 or as seen in FIG. 14.

Exposure control for the digital mammogram can be done using standard methods: manual and thickness-based exposure, and the Automatic Exposure Control (AEC) method. In AEC, a short (e.g., ~50 msec) low dose x-ray pulse is made and the image receptor's image is read by a computer process, which determines the breast area of greatest radiodensity and appropriately calculates the correct final x-ray tube exposure voltage kVp and current mAs so as to generate a properly exposed image.

When the systems illustrated in FIGS. 2 and 4 are operating in combo mode, and the tomosynthesis scan occurs after the mammogram, the system can use the mammogram exposure data to estimate the tomosynthesis exposure techniques. If the tomosynthesis scan is done at the same kVp as the digital mammogram, then the AEC information from the mammogram can be used to determine the tomosynthesis exposure values. In general, the tomosynthesis scans are performed at a different kVp from the digital mammogram. In this case, the system can still estimate the correct tube current mAs for each of the tomosynthesis images. This can be done through a lookup table means. The compressed breast thickness and some combination of the mammogram's kVp, mAs, and detector counts are used as lookup indices in a lookup table that outputs the tomo's kVp and mAs for each of the exposures. The look-up table can be generated in a manner known in the art by testing exposures using different x-ray thicknesses phantoms and different kVp and mAs, and observing resulting x-ray images.

Another method of performing exposure control in a tomosynthesis scan is the following. This method applies whether or not a digital mammogram is performed while the patient's breast remains immobilized, and can be used independent of the order the mammogram and tomosynthesis scan are performed. In this method, the tomosynthesis scan is started. The first tomosynthesis image is used to estimate the appropriate exposure factors for the remaining images in the tomosynthesis sequence, in a manner known from the AEC art. The first tomosynthesis image can either be included or excluded from the tomosynthesis reconstruction. The first tomosynthesis image can be done at a very low dose or else at a higher dose similar to the rest of the tomosynthesis images in the scan.

Similarly, if the mammogram is performed after the tomosynthesis acquisitions, one or more of the tomosynthesis images can be used to estimate the optimal kVp and mAs for the mammogram exposure, in place of the typical separate AEC pre-pulse needed for the mammogram, again using, for example, a computer-implemented look-up table derived through suitable testing of phantoms. In yet another embodiment, the mammogram can have its own AEC pre-pulse performed similarly as it is done when no tomosynthesis image is taken, i.e. just prior to the mammogram.

An important component of digital mammogram imaging relates to quality assurance of the image. Typically, the image is reviewed immediately following the acquisition, to ensure that the breast was properly positioned and visible in the image, that the exposure settings generated a high quality image, and that there is no patient motion that would blur the image. This is done by viewing what is known as the preview image.

In the case of the tomosynthesis scans described in this patent specification, and for combo mode acquisitions (both mammogram and tomosynthesis imaging using the same system) new types of preview images can be used. Following a tomosynthesis scan, there are several image sets that can be viewed to check for proper image quality. The projections, which are the typically (but not necessarily) 11 views taken of the breast from varying angles, can be viewed. Each one of these is a type of mammogram, albeit at lower dose than a conventional mammogram, and they can be reviewed like the preview image of a mammogram. These projections can be viewed singly, or by scrolling through them, or by displaying them dynamically as in a cine loop, or by displaying only a few of them at one time. The projections as displayed are not necessarily at the same resolution as the native images acquired. They might be on a coarser matrix than the image acquisition matrix of imager 16, which might be adequate for identifying image quality problems.

Alternatively, the projections can be reconstructed into the 3D dataset of tomosynthesis slice images, and the preview can take place using the reconstructed slices. These can also be viewed singly, or by scrolling through them, or by displaying them dynamically as in a cine loop, or by displaying only a few of them at a time. The reconstructed slices can be displayed at a different resolution compared to the final dataset sent to the display workstation where they are read by the radiologist making the diagnosis. The pixel spacing, slice separation, slice orientation, and slice thickness are other variables that can differ from the final dataset, although any of these might also be identical to the final dataset. One motivation for displaying a larger slice separation or coarser resolution (larger pixel spacing) in the tomosynthesis preview relative to the tomosynthesis final dataset is to be able to quickly reconstruct and preview the images.

A third approach is to display both the projections and the reconstructions. In this case, the two types of images can be on the display screens simultaneously or displayed one after the other.

In combo mode imaging, there will likely be a review of both the mammogram and the tomosynthesis images. The order in which they appear may depend upon whether or not the tomosynthesis images are taken first or last in the combo sequence, or alternatively the preview images of both might appear simultaneously. The tomosynthesis preview images can be any of the combinations described above for a tomosynthesis scan in non-combo mode.

In combo mode, another method of preview can involve overlay imaging. If the mammogram and the tomosynthesis image were acquired during the same compression, then the images should be capable of being co-registered in the absence of patient motion. Accordingly, an overlay method can be used in which the mammogram and the tomosynthesis slice images can be displayed on top of each other, simultaneously or alternating. If objects shift from one image to another, this may indicate patient motion. To facilitate this correlation, the tomosynthesis scan is preferably reconstructed into a cone beam projective geometry, as disclosed in commonly owned patent application No. 60/628,516, filed Nov. 15, 2004, which is hereby incorporated by reference.

The digital mammogram and the tomosynthesis images are taken of the same breast, however the acquisitions typically are done at different exposure techniques and the image processing can be quite different for these two different modalities. In particular, the optimal display settings such as window width & level might be different for these two different image sets. This would be the case for the preview images and for the final images displayed on the softcopy workstation.

Further improvements in a combo (mammography/tomosynthesis) system can be achieved by selective binning of the pixel data from imager 16. The system can operate at different spatial resolution of images, e.g. finer for mammograms and coarser for tomosynthesis images. The binning can be asymmetric within the tomosynthesis mode, e.g. coarser in the scanning direction and finer in the orthogonal direction. As a non-limiting example, imager 16 may have a native spatial resolution of a 70×70 micrometers pixel pitch. This may be the spatial resolution used for mammograms taken with the system. However, for tomosynthesis imaging, binning may be used by image processing unit 98 (FIG. 9) to reduce the spatial resolution. For example, the output of each set of 4 pixel positions in imager 16 may be averaged or otherwise combined into a single averaged pixel value for further image processing, thus forming an image corresponding to a spatial resolution at the imager of 140×140 micrometers. If the outputs of every three pixels are averaged or otherwise combined (e.g. with different weighting) in the scanning direction (in which the x-ray source moves relative to the immobilized breast) but the outputs of every two pixels are combined in the in the orthogonal direction, the result is effective spatial resolution of 140×210 micrometers. If four pixels are binned in the scanning direction but 2 in the orthogonal direction, the resulting effective resolution is 140×280 micrometers. Other binning combinations can be used in the alternative. The coarser resolution in the scanning direction can be effectively recovered somewhat by the acquisition and reconstruction process, where multiple views along the scanning direction contribute to a reconstructed pixel's value. The binning described above, which can differ between the direction of scan and the orthogonal direction is believed to be different in principle and in effect from that proposed in a patent by M. Stanton, Brandeis Univ. U.S. Pat. No. 6,744,848, which is understood to involve different binning for different angular positions of the x-ray source in a tomosynthesis scan. Programming suitable binning for use in image processor 98 is within the skill of the art once the information disclosed above is available.

The above specific embodiments are illustrative, and many variations can be introduced on these embodiments without departing from the spirit of the disclosure or from the scope of the appended claims. For example, elements and/or features of different illustrative embodiments may be combined with each other and/or substituted for each other within the scope of this disclosure and appended claims.

The invention claimed is:

1. A method of imaging a patient's breast with x-rays comprising:
   immobilizing a patient's breast between an x-ray source and a flat panel digital x-ray imager, said source comprising a focal spot from which an x-ray beam emanates;
   moving the focal spot through different imaging positions relative to the breast over a trajectory that is generally to one lateral side of a normal to a center of the imager when said trajectory includes a CC imaging position;
   imaging the breast with x-rays using the source and imager at each of said imaging positions; and
   providing a patient's head shield between the source and the imager, said shield being offset laterally relative to a normal to a center of the imager at a CC imaging position to reduce or eliminate cocking of the patient's head.

2. A method as in claim 1 which comprises taking mammogram image data at an imaging position that is at or is close to one lateral end of said trajectory.

3. A method as in claim 2 which comprises taking tomosynthesis image data at intermediate imaging positions along said trajectory.

4. A method as in claim 3 including using an anti-scatter grid between the breast and the imager when taking mammogram image data.

5. A method as in claim 3 including using an anti-scatter grid between the breast and the imager when taking tomosynthesis image data.

6. A method as in claim 1 which comprises taking mammogram image data at an imaging position that is closest to the patient's head along said trajectory.

7. A method as in claim 1 which comprises taking mammogram image data at an imaging position that is furthest from the patient's head along said trajectory.

8. A method as in claim 1 including taking mammogram image data at one of said imaging positions and tomosynthesis data at other ones of said imaging positions, and changing compression of a breast being imaged between taking image data and taking tomosynthesis image data.

9. A method as in claim 1 including taking mammogram image data at one of said imaging positions and tomosynthesis data at other ones of said imaging position, and using a computer-implemented lookup table for exposure control that relates exposure factors for acquiring mammogram image data to exposure factors for acquiring tomosynthesis image data.

10. A method as in claim 1 including taking tomosynthesis data at each of a plurality of said imaging positions, and using tomosynthesis data taken at a starting imaging position to determine x-ray exposure at subsequent ones of said imaging positions.

11. A method as in claim 1 including taking tomosynthesis data at each of a plurality of said imaging positions and using the tomosynthesis data to computer-reconstruct tomosynthesis images of slices of the patient's breast.

12. A method as in claim 11 including selectively determining a thickness of said slices.

13. A method as in claim 11 including selectively determining an orientation of said slices.

14. A method as in claim 11 including displaying at least selected ones of said tomosynthesis images in a preview mode as preview tomosynthesis images.

15. A method as in claim 14 including taking mammogram data at one of said imaging positions and processing the mammogram image data into a preview mammogram image and selectively displaying the preview mammogram image and said preview tomosynthesis images.

16. A method as in claim 15 comprising displaying the preview tomosynthesis images before displaying the preview mammogram image.

17. A method as in claim 15 comprising displaying said preview mammogram image before displaying said preview tomosynthesis images.

18. A method as in claim 15 comprising concurrently displaying the mammogram and tomosynthesis preview images.

19. A method as in claim 15 in which one or more of the mammogram preview image and tomosynthesis preview images are displayed at window and/or width levels different from those of others of said preview images.

20. A method as in claim 15 in which one or more of the mammogram preview image and tomosynthesis preview images are displayed at spatial resolution different from that of others of said preview images.

21. A method as in claim 15 including reconstructing said mammogram and tomosynthesis image data into respective final images that differ from the respective preview images in at least one of spatial resolution and spacing of displayed tomosynthesis images.

22. A method as in claim 1 wherein the shield shields the patient's head from the moving x-ray source.

23. A method as in claim 22 in which the shield is below the x-ray source when the source is in position for a CC mammogram.

24. A method as in claim 23 including moving the shield laterally between miaging the patient's left breast and the patient's right breast.

25. A method as in claim 1 including spacing the focal spot of the x-ray source from an imaging plane the imager by a distance SID that equals or exceeds 70 cm.

26. A method as in claim 25 including providing a shield that shields the patient's head from the moving x-ray source, wherein said source moves relative to said shield when moving through said imaging positions.

27. A method as in claim 26 in which the shield is between the x-ray source and the patient's breast, and to one side of the patient's head, when the source is in a CC position.

28. A method as in claim 27 including moving the shield laterally between CC imaging of the patient's left breast and CC imaging of the patient's right breast to reduce or eliminate cocking the patient's head.

29. A method as in claim 1 including performing automatic exposure control by using tomosynthesis image data derived at one or more of said imaging positions to determine exposure information for mammogram image data derived at another of said imaging positions.

30. A method as in claim 1 including deriving tomosynthesis image data comprising respective pixel values at least at some of said imaging positions and binning said pixel values by selectively combining them into a lesser total number of combined pixel values.

31. A method as in claim 30 in which said combining is asymmetric in that fewer pixel values are combined into a respective combined pixel values in one direction in an image plane in the imager than in another direction.

32. A method as in claim 31 in which a greater number of pixel values are combined into respective combined pixel values in the direction of motion of the x-ray source than in an orthogonal direction.

33. A method as in claim 1 in which the focal spot moves away from the patient's head along said trajectory.

34. A method as in claim 1 in which the focal spot moves toward the patient's head along said trajectory.

35. A system as in claim 34 in which the distance between the focal spot in the source and an imaging plane in the imager equals or exceeds 70 cm.

36. A system for imaging a patient's breast with x-rays comprising:
  a flat panel digital x-ray imager and an x-ray source that comprises a focal spot from which an x-ray beam emanates when the source is energized;
  a breast support and compression paddle immobilizing a patient's breast between the x-ray source and the x-ray imager;
  a motorized gantry selectively moving the focal spot through different imaging positions relative to the breast, over a trajectory that is generally to one side of a normal to a center of the imager when said trajectory includes a CC imaging position;
  an imaging control selectively energizing the source and imager to image the breast with x-rays using the source and imager at each of said imaging positions; and
  a patient's head shield between the source and the imager, said shield being offset laterally relative to a normal to a center of the imager at a CC imaging position to reduce or eliminate cocking of the patient's head.

37. A system as in claim 36 in which said motorized gantry moves said focal spot away from the patient's head along said trajectory.

38. A system as in claim 36 in which said motorized gantry moves said focal spot toward the patient's head along said trajectory.

39. A system for imaging a patient's breast with x-rays comprising:
  an x-ray source and a flat panel digital x-ray imager;
  a breast support and compression paddle immobilizing a patient's breast between the x-ray source and the x-ray imager;
  a motorized gantry selectively moving the source through different imaging positions relative to the breast;
  a shield for the patient's head, said shield being below the source and offset laterally from a normal to a center of the imager when the source is in a CC imaging position, and said source clearing the shield when moving through said different imaging positions.

* * * * *